US012144496B2

(12) United States Patent
Sauer et al.

(10) Patent No.: US 12,144,496 B2
(45) Date of Patent: *Nov. 19, 2024

(54) STERNAL ASCENDER APPARATUS

(71) Applicant: LSI Solutions, Inc., Victor, NY (US)

(72) Inventors: Jude S. Sauer, Pittsford, NY (US); Matthew David DeClerck, Greece, NY (US); Angelo John Martellaro, Victor, NY (US); Benjamin James Boseck, Canandaigua, NY (US); Matthew Wrona, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/143,193

(22) Filed: May 4, 2023

(65) Prior Publication Data

US 2023/0270429 A1     Aug. 31, 2023

Related U.S. Application Data

(63) Continuation of application No. 16/999,838, filed on Aug. 21, 2020, now Pat. No. 11,666,317.

(60) Provisional application No. 62/989,044, filed on Mar. 13, 2020, provisional application No. 62/916,591, filed on Oct. 17, 2019, provisional application No. 62/889,690, filed on Aug. 21, 2019.

(51) Int. Cl.
*A61B 17/00*     (2006.01)
*A61B 17/02*     (2006.01)

(52) U.S. Cl.
CPC ...... *A61B 17/025* (2013.01); *A61B 17/00234* (2013.01); *A61B 2017/00243* (2013.01); *A61B 2017/00455* (2013.01)

(58) Field of Classification Search
CPC ................ A61B 17/0281; A61B 2017/0237
See application file for complete search history.

(56) References Cited

U.S. PATENT DOCUMENTS

| 1,919,455 | A | | 7/1933 | Wilson | |
|---|---|---|---|---|---|
| 3,196,865 | A | * | 7/1965 | Rose | A61B 17/02 600/230 |
| 5,052,373 | A | * | 10/1991 | Michelson | A61B 17/0206 600/234 |
| 5,795,291 | A | * | 8/1998 | Koros | A61B 17/02 600/231 |

(Continued)

OTHER PUBLICATIONS

PCT Search Report and Written Opinion for PCT/US2020/47440, International filing date Aug. 21, 2020, 9 pages, mailed Feb. 10, 2021.

(Continued)

*Primary Examiner* — Nicholas W Woodall
(74) *Attorney, Agent, or Firm* — Michael E. Coyne

(57) ABSTRACT

A sternal elevator apparatus is disclosed. The sternal elevator may include a panel, a support beam traversing the panel, and a post coupled to a proximal end of the panel. The apparatus may also include an indicator handle coupled to the sternal elevator, an actuator drive pivotably coupled to the indicator handle, and a housing movably coupled to the actuator drive. The sternal elevator apparatus may have an actuator drive incorporating a linear rack. The housing further may include a cylindrical gear where the cylindrical gear is engaged with the linear rack.

15 Claims, 16 Drawing Sheets

(56) References Cited

U.S. PATENT DOCUMENTS

| | | | | |
|---|---|---|---|---|
| 5,846,191 | A | 12/1998 | Wells et al. | |
| 6,042,542 | A * | 3/2000 | Koros | A61B 17/02 |
| | | | | 600/231 |
| 7,909,846 | B1 | 3/2011 | Taylor et al. | |
| 8,974,381 | B1 | 3/2015 | Lovell et al. | |
| 9,113,853 | B1 | 8/2015 | Casey et al. | |
| 9,335,782 | B2 * | 5/2016 | Koros | G05G 1/082 |
| 2005/0148824 | A1 | 7/2005 | Morejohn et al. | |
| 2005/0159651 | A1 | 7/2005 | Raymond et al. | |
| 2007/0238932 | A1 | 10/2007 | Jones et al. | |
| 2010/0312069 | A1 | 12/2010 | Sutherland et al. | |
| 2017/0239048 | A1 | 8/2017 | Goldfarb et al. | |
| 2020/0015801 | A1 * | 1/2020 | Sauer | A61B 17/02 |

OTHER PUBLICATIONS

Chanoit et al., Retraction mechanics of Finochietto-style self-retaining thoracic retractors, BioMedical Engineering OnLine, 18, Article No. 45, 35 pages, Jul. 19, 2021.

Extended European Search Report for EP Application No. 20855514. 4, dated Jul. 4, 2023, 10 pages.

* cited by examiner

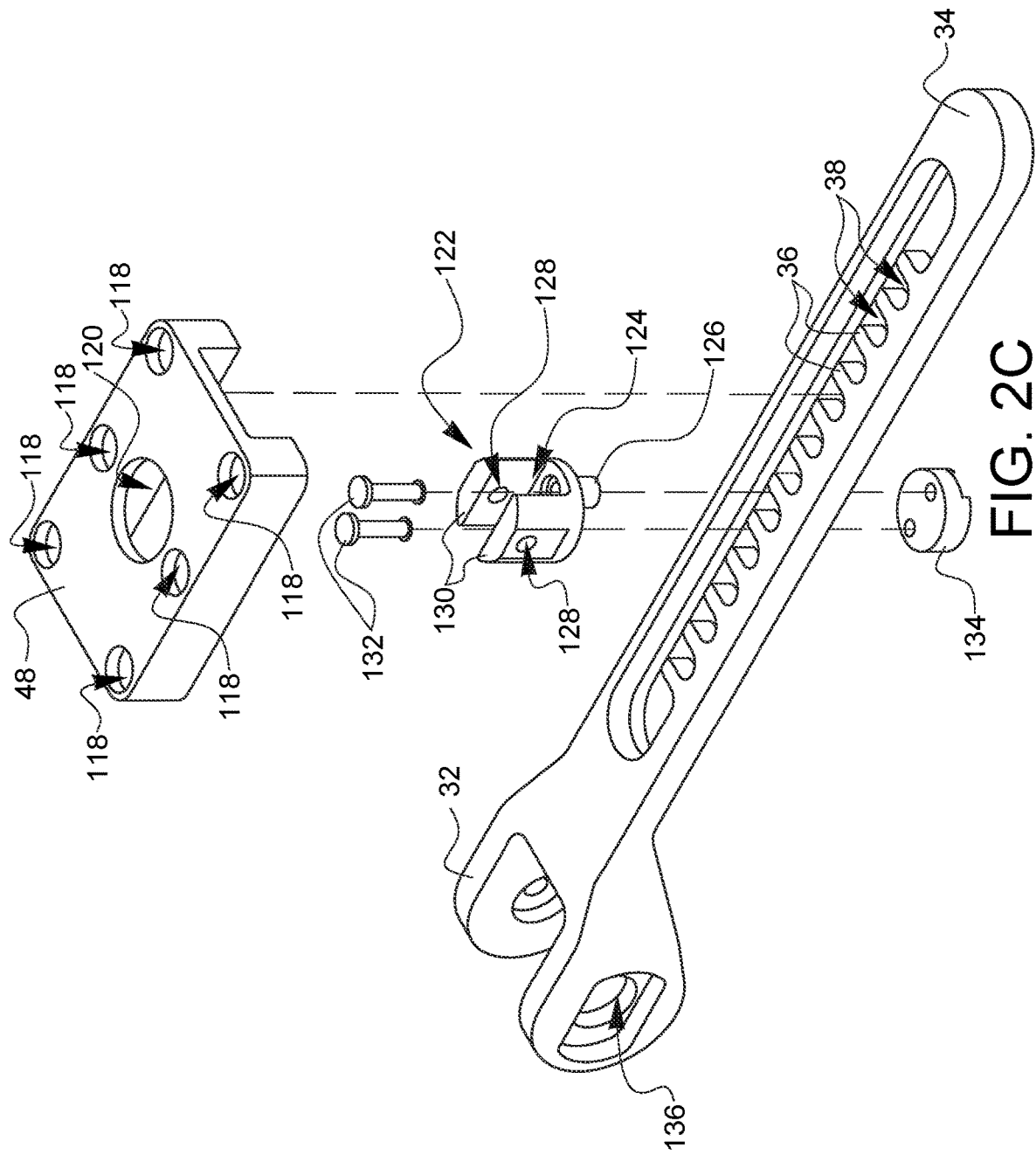

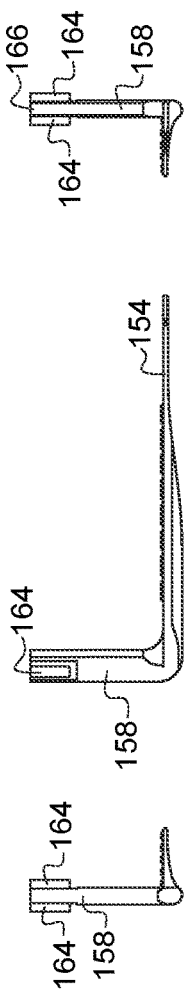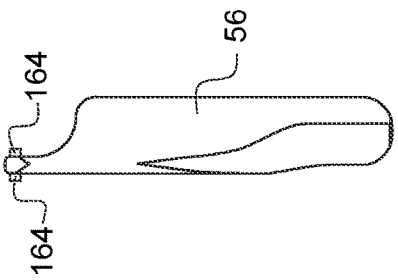

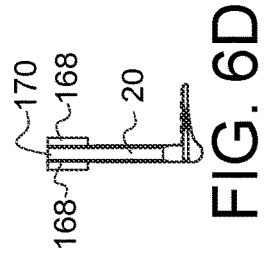
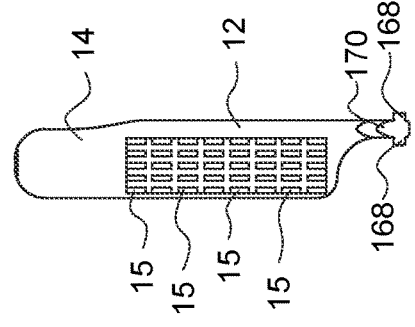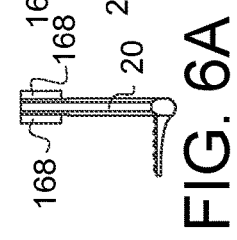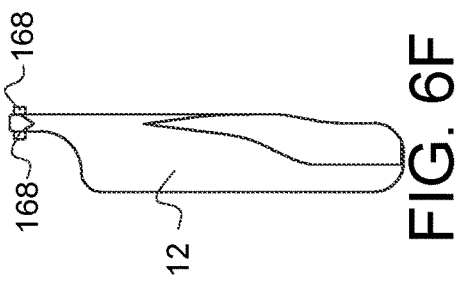
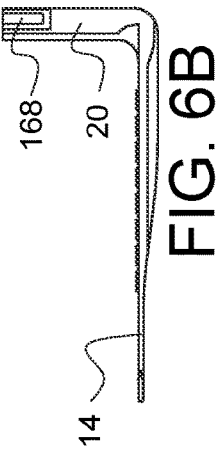

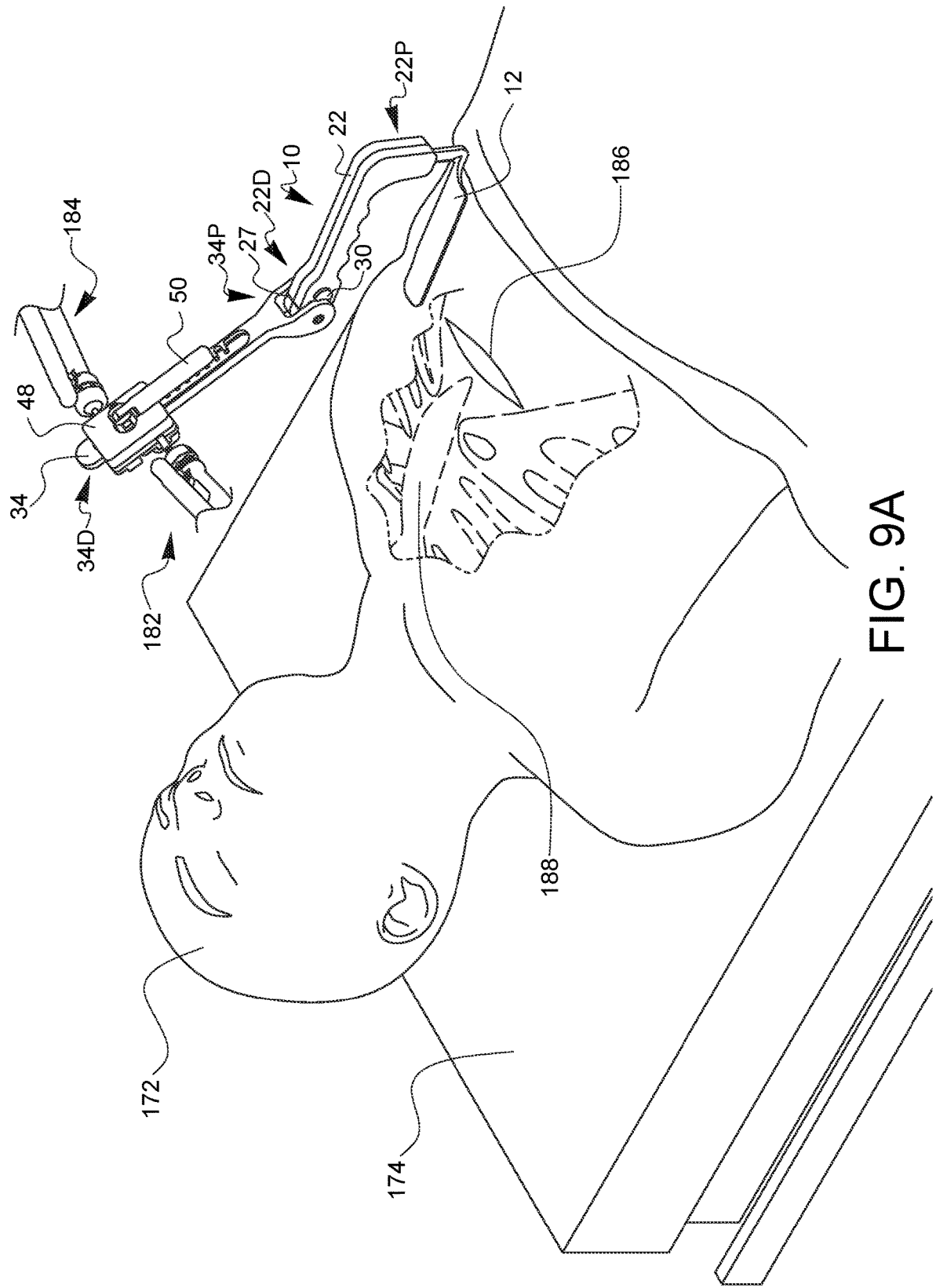

STERNAL ASCENDER APPARATUS

REFERENCE TO RELATED APPLICATIONS

This patent application is a continuation of U.S. patent application Ser. No. 16/999,838, filed Aug. 21, 2020, which claims priority to U.S. Provisional Patent Application No. 62/889,690, filed Aug. 21, 2019, U.S. Provisional Patent Application No. 62/916,591, filed Oct. 17, 2019, and U.S. Provisional Patent Application No. 62/989,044, filed Mar. 13, 2020, each of which is hereby incorporated by reference in its entirety.

FIELD

The claimed invention relates to minimally invasive surgical devices, and more specifically to a surgical device used in increasing operable space during minimally invasive surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, visualization, maintenance of insufflation, and distal suturing of a coronary anastomosis in totally endoscopic coronary artery bypass grafting on the beating heart is technically demanding. There is a need for larger working spaces to accommodate an increased range of motion during surgical procedures, as well as room for additional surgical tools, such as endoscopes, suturing tools, and the like. However, achieving an increased working space should ideally preserve chest wall integrity and avoid CPB. Likewise, a minimally invasive surgical approach should not compromise the reliability of a cardiac repair.

Therefore, there exists a need for minimally invasive surgical devices and methodology applicable to ITA harvesting and other surgical procedures such as epicardial lead placement and others that increase operable space for harvesting and anastomosis and other surgical procedures, reduce operating time, and improve patient outcome during minimally invasive cardiac procedures and other surgical procedures.

BRIEF DESCRIPTION OF THE DRAWINGS

FIGS. 2A-2E is a series of exploded views illustrating the apparatus of the sternal ascender apparatus of FIG. 1.

FIGS. 4A, 4B, 4C, 4D, 4E, and 4F are front, left side, right side, rear, top, and bottom elevational views, respectively, of the sternal ascender of FIG. 3.

FIGS. 6A, 6B, 6C, 6D, 6E, and 6F are front, left side, right side, rear, top, and bottom elevational views, respectively, of the right sternal ascender of FIG. 5.

FIGS. 9A-9D are a series of perspective views illustrating operational steps of the use of the sternal ascender apparatus in a surgical context.

Figure 1:
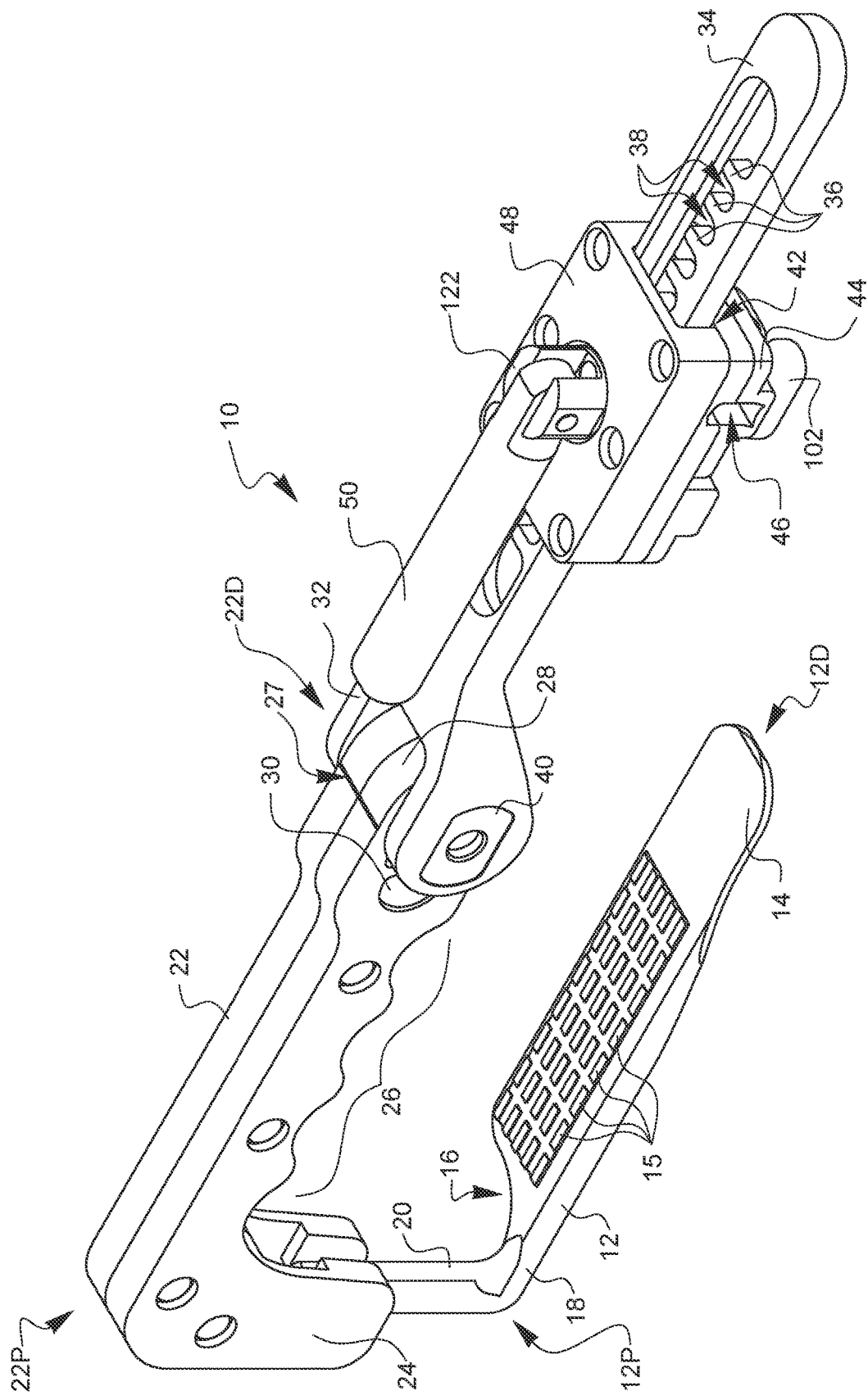
FIG. 1 is a top-front-right perspective view of one embodiment of a sternal ascender apparatus with a right sternal ascender attached.

It will be appreciated that for purposes of clarity and where deemed appropriate, reference numerals have been repeated in the figures to indicate corresponding features, and that the various elements in the drawings have not necessarily been drawn to scale in order to better show the features.

SUMMARY

A sternal ascender apparatus is disclosed. The sternal ascender may include a panel, a support beam traversing the panel, and a post coupled to a proximal end of the panel. The apparatus may also include an indicator handle coupled to the sternal ascender, an actuator drive pivotably coupled to the indicator handle, and a housing movably coupled to the actuator drive. The sternal ascender apparatus may have an actuator drive incorporating a linear rack. The housing further may include a cylindrical gear where the cylindrical gear is engaged with the linear rack.

Another sternal ascender apparatus is disclosed. The sternal ascender may include a panel having a plurality of textural features, a support beam traversing the panel, and a post coupled to a proximal end of the panel. The apparatus may also include an indicator handle removably coupled to the sternal ascender, an actuator drive pivotably coupled to the indicator handle having a linear rack, and a housing movably coupled to the actuator drive having a cylindrical gear and two instrument adapters.

DETAILED DESCRIPTION

FIG. 1 is a perspective view of one embodiment of a sternal ascender apparatus with a right sternal ascender attached. An embodiment of a sternal ascender apparatus 10 is shown in FIG. 1, with a right sternal ascender 12 installed therein. The right sternal ascender 12 defines a panel 14, the panel 14 having several textural features 15 configured to provide an atraumatic yet firm grip on the underside of a ribcage when the sternal ascender assembly 10 is in use in a minimally invasive surgical procedure. The panel 14 of the right sternal ascender 12 also defines a notch 16 and has a support beam 18 on the underside of the panel 14 The right sternal ascender 12 has a mounting post 20 on a proximal end 12P. The mounting post 20 is coupled to a proximal end 22P of an indicator handle 22 at the end of the mounting portion 24 of the indicator handle 22. The right sternal ascender 12 is coupled by reversible means such that the right sternal ascender 82 may be easily removed and replaced with a left sternal ascender, which is not shown in this view. The term ascender may be used interchangeably with the term elevator or lifter, as they equivalently describe the intended function of the ascender and associated apparatus. This coupling means will be described in further detail later. One alternate example of a coupling method is using a set screw, although others may be known to those skilled in the arts. The indicator handle 22 further defines a grip 26 in the underside of the indicator handle 22, which is configured for an ergonomic gripping feature for the comfort of use by a surgeon. At a distal end 22D of the indicator handle 22 is a connection end 28 and a pressable switch 30. Towards the distal end 22D of the indicator handle 22 is a depth indication mark 27, which is vertically aligned with the distal end 12D of the right sternal ascender 12. The connection end 28 is a coupling point that accepts a corresponding connection end 32 on a linear rack or linear actuator gear 34 by way of mating with the connection end 28 and is pivotably attached by joining a pivot pin 40 or alternatively by other attachment means into a hole or other attachment means not shown in this view. The pressable switch 30 can be pressed or actuated to defeat a pawl that is located inside the indicator handle 22, but not shown in this view. The pawl interfaces with a fixed indexing gear located inside the connection end 32 portion of the linear actuator gear 34. This will be discussed later in more detail in regard to FIGS. 2A-2E. The pawl defines a spring or biasing element to bias, while at rest, one or more teeth defined by the pawl toward the fixed indexing gear, which is not shown in this view but is coupled to the connection end 32 of the linear actuator gear 34. When the one or more teeth on the pawl intermesh with one or more corresponding teeth or other locking feature defined by the fixed indexing gear, this locks the angular position of the linear actuator gear 34 relative to the position of the indicator handle 22. When switch 30 is pressed or actuated, the pawl is defeated and temporarily pushed away from the fixed indexing gear, allowing free angular movement of the linear actuator gear 34 relative to the indicator handle 22. Releasing the switch 30, re-engages the pawl and the fixed indexing gear to once again interface and lock the angular position of the linear actuator gear 34 relative to the indicator handle 22 that it was in when the switch 30 was released.

The linear actuator gear 34 further defines several teeth 36 and several recesses 38 that engage a cylinder gear 122. The linear actuator gear 34 fits through an actuator slot 42 in a dual side instrument adapter 44. The dual side instrument adapter 44 defines a first adapter channel 46 and a second adapter channel, not visible here, on the opposite side. The dual side instrument adapter 44 also defines several locking mechanisms 100, 102 for locking the dual side instrument adapter 44 into a surgical equipment holder on each side. Once the dual side instrument adapter 44 is attached on each side to a surgical equipment holder, it can be positioned over a patient by bridging two surgical equipment holders across a surgical table. Other embodiments may only have a single adapter channel for mounting onto a single surgical equipment holder. Attached to the dual side instrument adapter 44 is a gear housing 48 which holds the cylinder gear 122. A handle or swivel bar 50 is coupled to the cylinder gear 122. Turning the handle 50 rotates the cylinder gear 122 and thereby moves the linear actuator gear 34 back and forth which forms an actuator drive. In this embodiment, the sternal ascender assembly 10 is inserted into an incision below the sub-xiphoid of a patient undergoing a minimally invasive surgical procedure, such as an ITA harvesting procedure or other surgical procedure in which increased access space below the sub-xyphoid process is advantageous. The panel 14 of the right sternal ascender 12 can be used to enable lifting the ribcage, thereby increasing space in the subxiphoid area. One feature of the sternal ascender assembly 10 is that the length of the distal end 22D of the indicator handle 22 is substantially the same as the length of the right sternal ascender 12 panel 14, which provides the surgeon with a visible indication, along with the depth indication mark 27 of how far the right sternal ascender 12 or the right sternal ascender (if installed into the sternal ascender apparatus 10) has been inserted into the subxiphoid cavity of the patient. The distal end 22D of the indicator handle 22 is substantially aligned with a distal end 12D of the sternal ascender 12. The indicator handle 22 is also substantially parallel to the panel 14 of the right sternal ascender 12 or the panel of a right sternal ascender. Once the sternal ascender apparatus or assembly 10 is inserted into the subxiphoid cavity, the sternal ascender assembly 10 is attached to one or more surgical equipment holders, enabling stability of force throughout a minimally invasive surgical procedure. Further adjustments to the position of the sternal ascender assembly 10 may then be made by pivoting about the coupling joint of the indicator handle 22 and the linear actuator gear 34. The sternal ascender assembly 10 can be further adjusted by rotating the swivel bar 50 and actuating the linear actuator gear 34 in a distal direction. This operation will be discussed in further detail later.

Figure 2A:
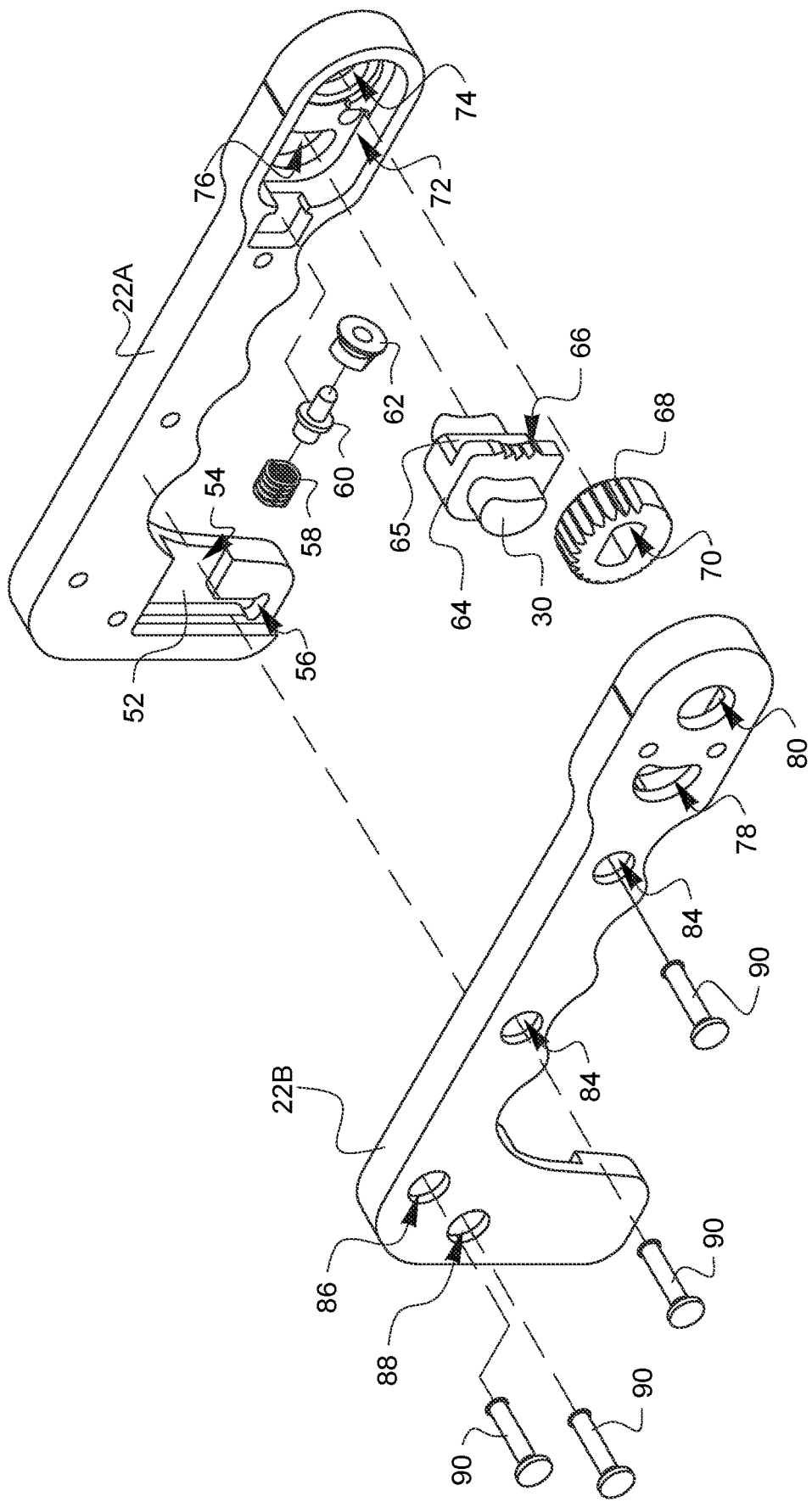

FIGS. 2A-2E is a series of exploded views illustrating the assembly of the sternal ascender apparatus of FIG. 1. As illustrated in FIG. 2A, a first handle half 22A defines a recess or channel 52 having a mounting slot 54 and a seat 56. The mounting slot 54 and seat 56 defined by the channel 52, also referred to as a t-slot based on the general shape thereof, are configured to removably receive an alignment key on the post of either a left or right sternal ascender. A second handle half 22B also defines a corresponding recess, not shown in this view. The first handle half 22A also defines a second recess 72 at an opposite end and a gear recess 74 and hole 76. The second handle half 22B also defines a corresponding recess, not shown in this view. The second recess 72 is configured to receive and hold a spring 58, spring plunger 60, and plunger housing 62, which are first assembled together. A pawl gear 64 having gears 66 and an ungeared portion 65 and a fixed indexing gear or a pivot gear 68 having a gear keyway 70 are placed into hole 76 and held in gear recess 74, respectively, on the first handle half 22A. The pawl gear 64 is held against the spring 58, spring plunger 60, and plunger housing 62 assembly such that the pawl gear 64 is biased against the pivot gear 68 until the pawl gear 64 is depressed to slide the pawl gear 64 so that the gears 66 are disengaged from the pivot gear 68 such that it interfaces with the ungeared portion 65 of the pawl gear 64, thus allowing free rotation or pivoting of the pivot gear 68. When the pawl gear 64 is released, the gears 66 relock with the pivot gear 68 preventing further pivoting or rotation of the pivot gear

68. The second handle half 22B is then placed over the first handle half 22A and fastened using several rivets 90 which are placed and fixed into holes 84, 86, 88 on the second handle half 22B. While holes and rivets are used here to fixedly attach the handle halves 22A, 22B together, welding, adhesives or other means known to those skilled in the art may also be employed.

Figure 2B:
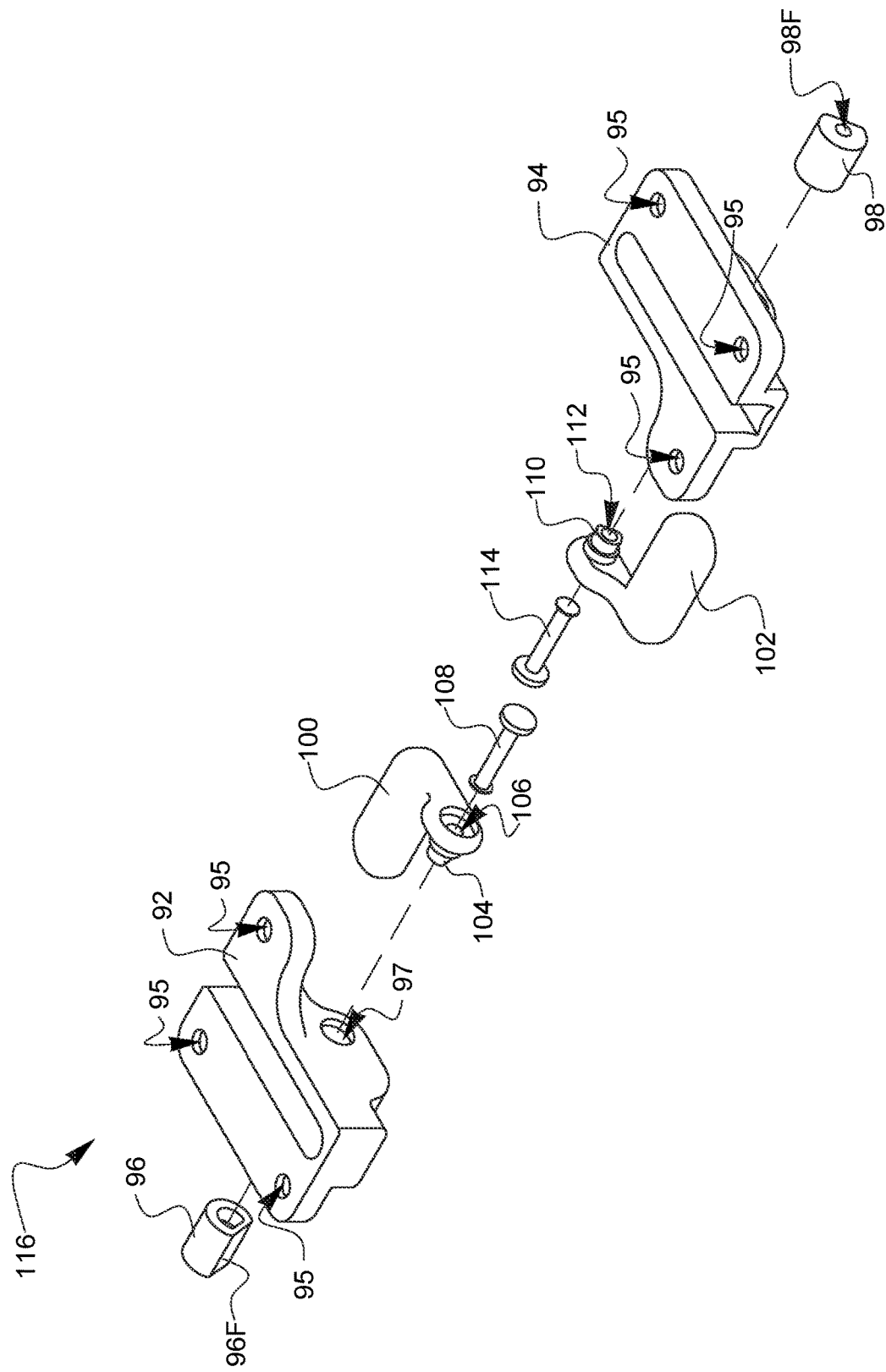

FIG. 2B illustrates the assembly of an instrument adapter assembly 116 portion of the sternal ascender apparatus 10. A first adapter housing 92 having several holes 95 and side hole 97 is assembled by placing a first cam 96 having a flat 96F into hole 97. A first lever lock 100 having a key 104 is placed into hole 97 and into the first cam 96 such that rotating the first lever lock 100 will also rotate the first cam 96 within hole 97. The first lever lock 100 is pivotably attached to the first adapter housing 92 with the use of rivet 108 being placed into channel 106 on the first lever lock 100. A second adapter housing 94 having several holes 95 and side hole, not visible here, is assembled by placing a second cam 98 having a flat 98F into hole 97. A second lever lock 102 having a key 110 is placed into a hole on the second adapter housing 94 and into the second cam 98 such that rotating the second lever lock 102 will also rotate the second cam 98 within the hole in the second adapter housing 94. The second lever lock 102 is pivotably attached to the second adapter housing 94 with the use of rivet 114 being placed into channel 112 on the second lever lock 102.

Figure 2D:
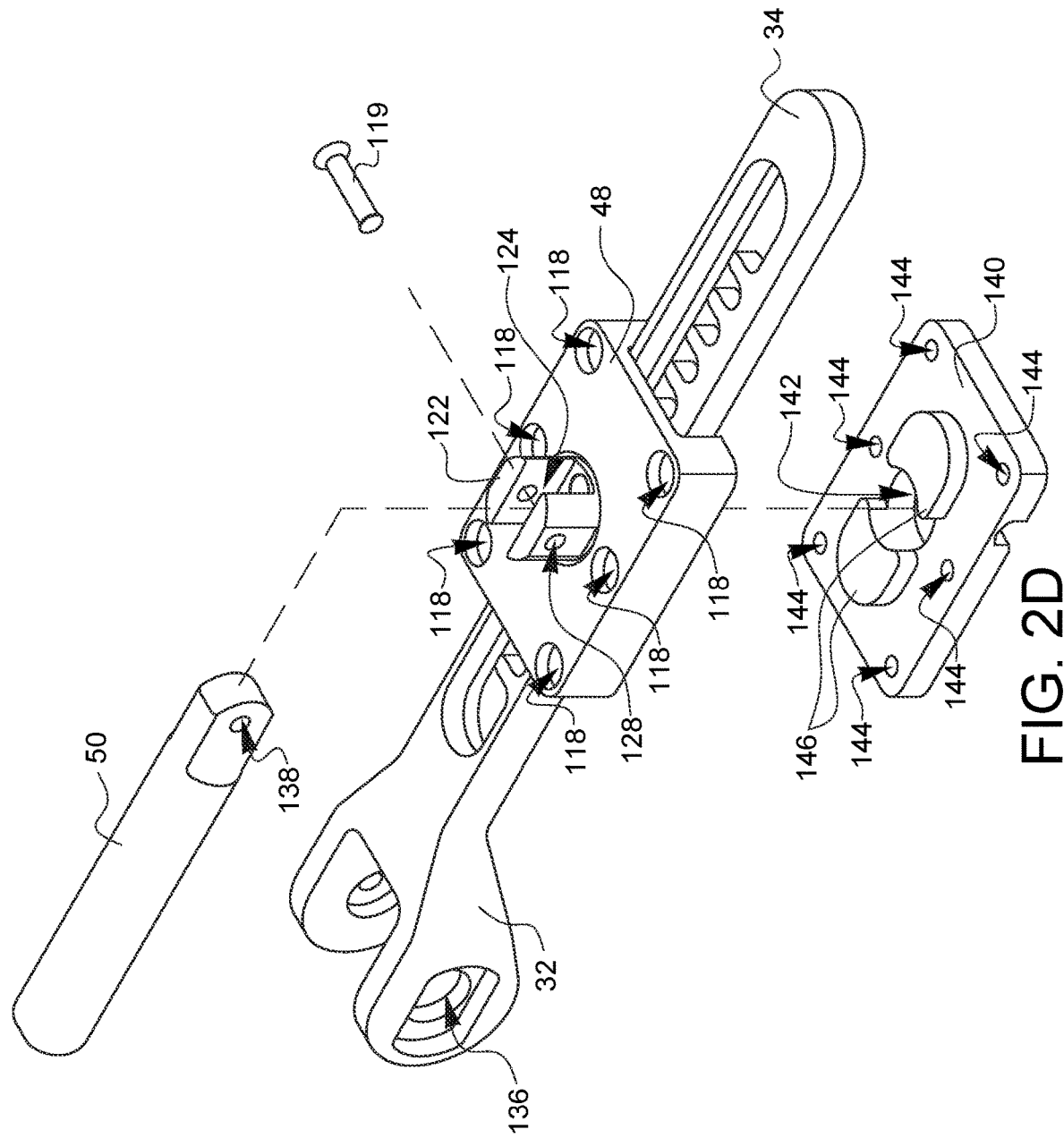
Figure 2E:
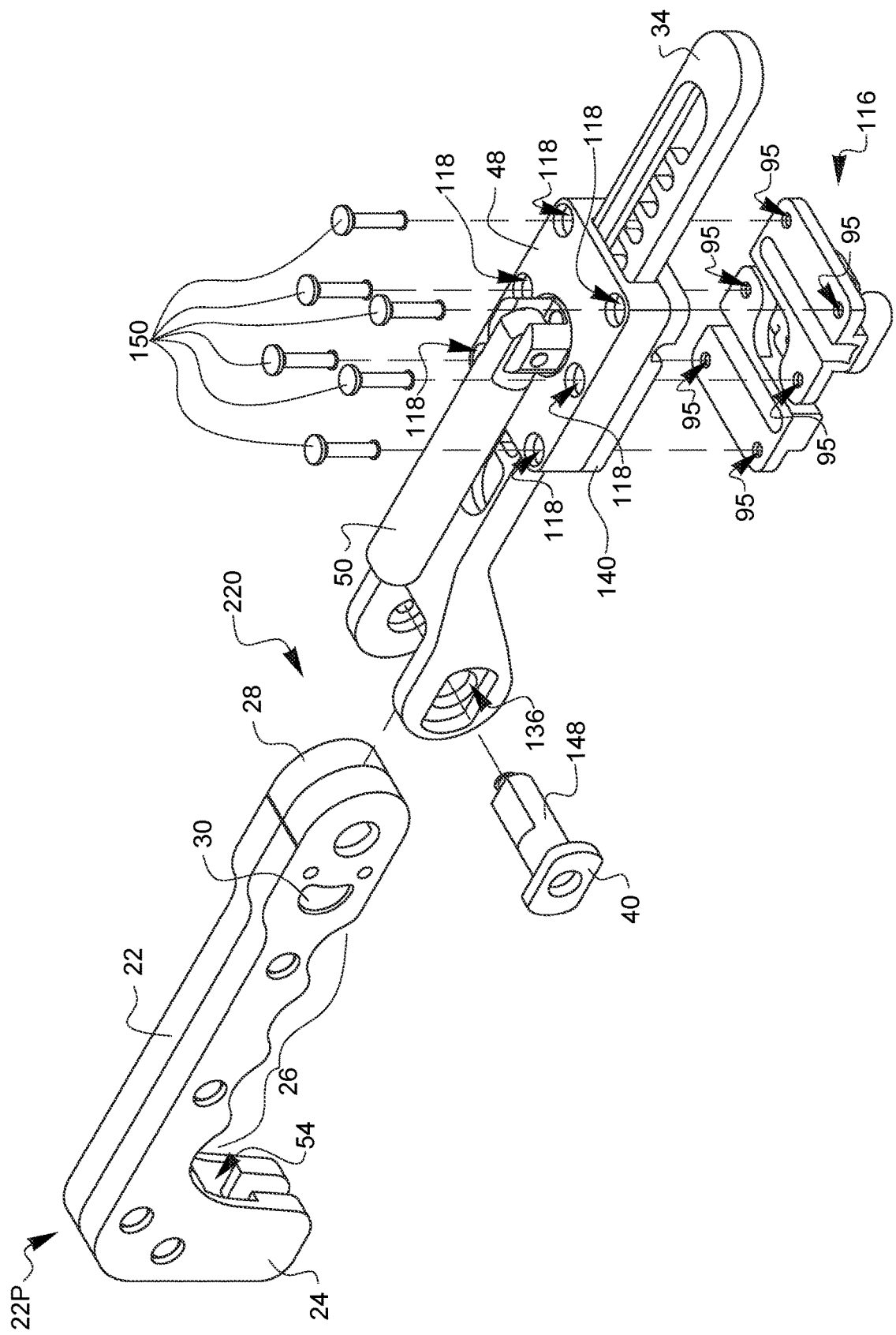

FIG. 2C continues the assembly of the sternal ascender apparatus 10 focusing on the linear actuator gear 34. The linear actuator gear 34, having a connection end 32 which further defines a hole 136 and several teeth 36 with several recesses 38 positioned therebetween. A cylinder gear 122 defines two sides 130, a side channel 128 on either side 130, a slot 124, and two posts 126, one of which is visible here, is placed into the linear actuator gear 34 with the two posts 126 held in two adjacent recesses 38. A drive bottom 134 is fixed with two rivets 132 onto the two posts 126 of the cylinder gear 122 on the opposite side of the linear actuator gear 34. Once fully assembled, the cylinder gear 122 is rotated in a clockwise or counterclockwise direction this thereby moves the linear actuator gear back and forth forming an actuator drive. As the cylinder gear 122 is rotated, the first pinion or post 126 will rotate out of a recess 38 on the linear actuator gear 34 and outward while the second pin driver (not visible here) remains in a second recess 38 and rotates within the second recess 38. The first post 126 will rotate into a third recess 38, past the second recess 38 thus translating rotational motion into linear motion and moving the linear actuator gear 34 relative to the gear housing 48. Performing this operation in the reverse will move the actuator gear 34 in the reverse direction. A upper rack housing 48 having a central opening 120 and several holes 118 is then placed over the linear actuator gear 34 and cylinder gear 122 so that the cylinder gear 122 protrudes from the central opening 120 of the upper rack housing 48 and the upper rack housing 48 is able to slide along the linear actuator gear 34 as the cylinder gear 122 is rotated. FIG. 2D illustrates the handle 50 being placed into the cylinder gear 122 between the two sides 130 and held in place by placing a rivet 119 through the side channels 128 on the cylinder gear 122 and through the hole 138 on the swivel bar 50. A middle rack housing 140 having a central hole 142, several holes 144, and two housing inserts 146 is placed onto the bottom of the linear actuator gear 34 to align with the upper rack housing 48. The holes 118 on the upper rack housing 48 are aligned with the holes 144 on the middle rack housing 140. The two housing inserts 146 are configured to hold captive and allow free rotation of the drive bottom 134 of the cylinder gear 122. The handle or swivel bar 50 is used to swivel and rotate the cylinder gear 122 during operation. The assembly of the sternal ascender apparatus 10 is completed in FIG. 2E by inserting the distal end 22D of the indicator handle 22 into the linear actuator gear 34. The pivot pin 40 is inserted into hole 136 with the pivot pin post 148 interlocking into the gear keyway 70 of the pivot gear 68, the function of which was illustrated in FIG. 2A. The instrument adapter assembly 116 shown and described in regard to FIG. 2B is placed onto the bottom of the middle rack housing 140 and holes 95 in the instrument adapter assembly 116 are aligned with the corresponding 118 holes in the upper rack housing 48. Several rivets 150 are then placed into the holes 118 to fixedly join the instrument adapter assembly 116 to the middle rack housing 140 and upper rack housing 48.

Figure 3:
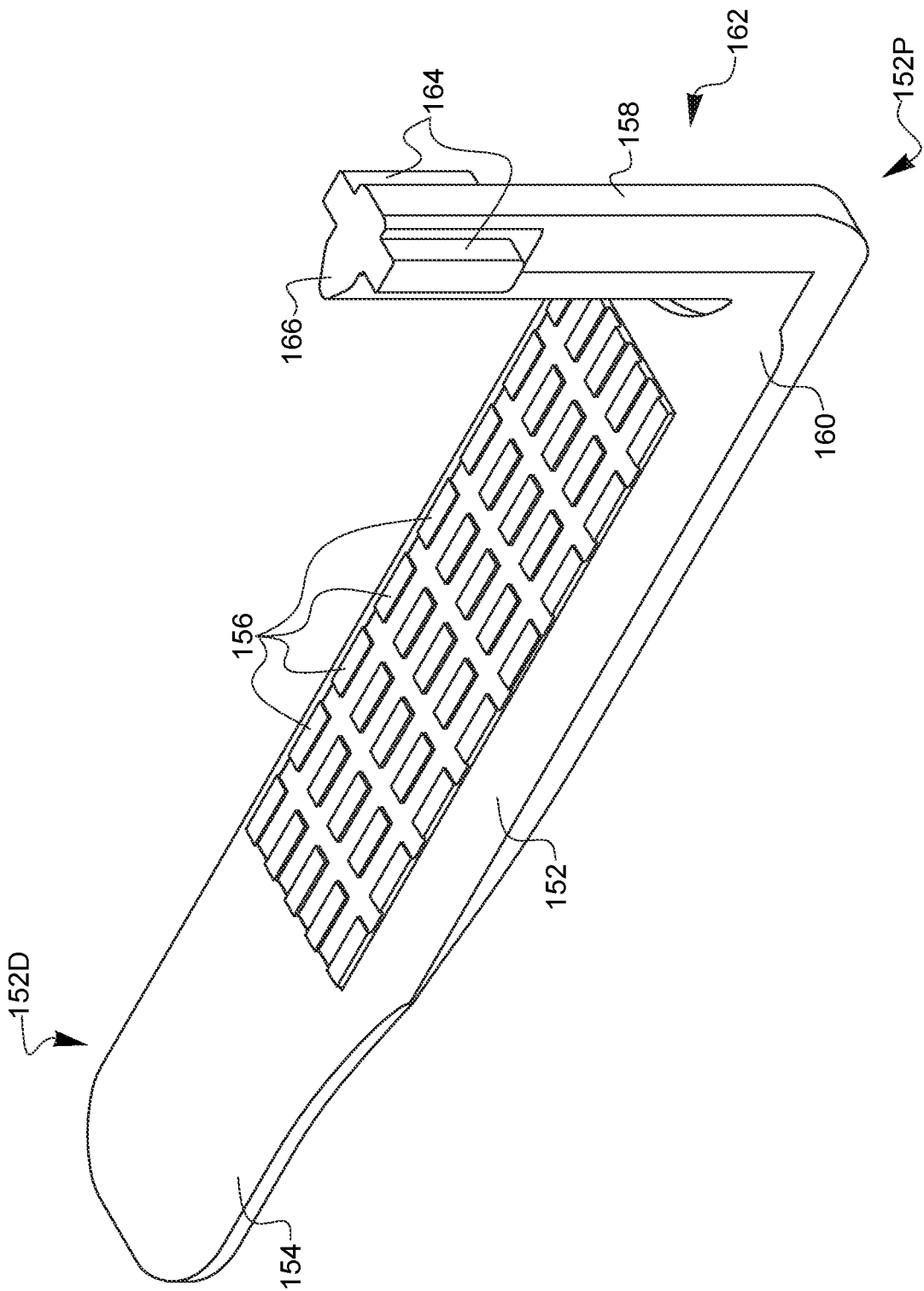
FIG. 3 is a perspective view of a left sternal ascender.

FIG. 3 is a perspective view of a left sternal ascender. This view illustrates the various features defined by the left sternal ascender 152. The left sternal ascender 152 defines a panel 154 having several textural features 156, a contralateral, or pertaining to the opposite side of targeted anatomical area, notch 162 at a proximal end 152P, a support beam 160 traversing the underside of the panel 154, and a mounting post 158 for attachment to a sternal ascender apparatus. The panel 154 has a rounded shape with a slight edge at a distal end 152D of the panel 154 of the left sternal ascender 152. Also defined by the post 158 are two opposing alignment and orientation features 164 configured to align, slide and lock the left sternal ascender 152 into the handle. These features 164 form a general t-shape, which are configured to fit into the aforementioned t-slot on the indicator handle 22. The use of this feature will be described further in regard to FIGS. 7A-7C. The post 158 also defines an angular front alignment feature 166 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments of a sternal ascender panel may have other shapes or radiuses, and may or may not be sharpened. Still other embodiments may have other features aside from the rectangular textural features 156 shown here, and may include other shaped features or none at all. Other embodiments of left sternal ascenders may be made of metal, plastic, composites, or mixtures or conbinations thereof or contain alternate alignment or locking methods and features. FIGS. 4A, 4B, 4C, 4D, 4E, and 4F are front, left side, right side, rear, top, and bottom elevational views, respectively, of the sternal ascender of FIG. 3.

Figure 5:
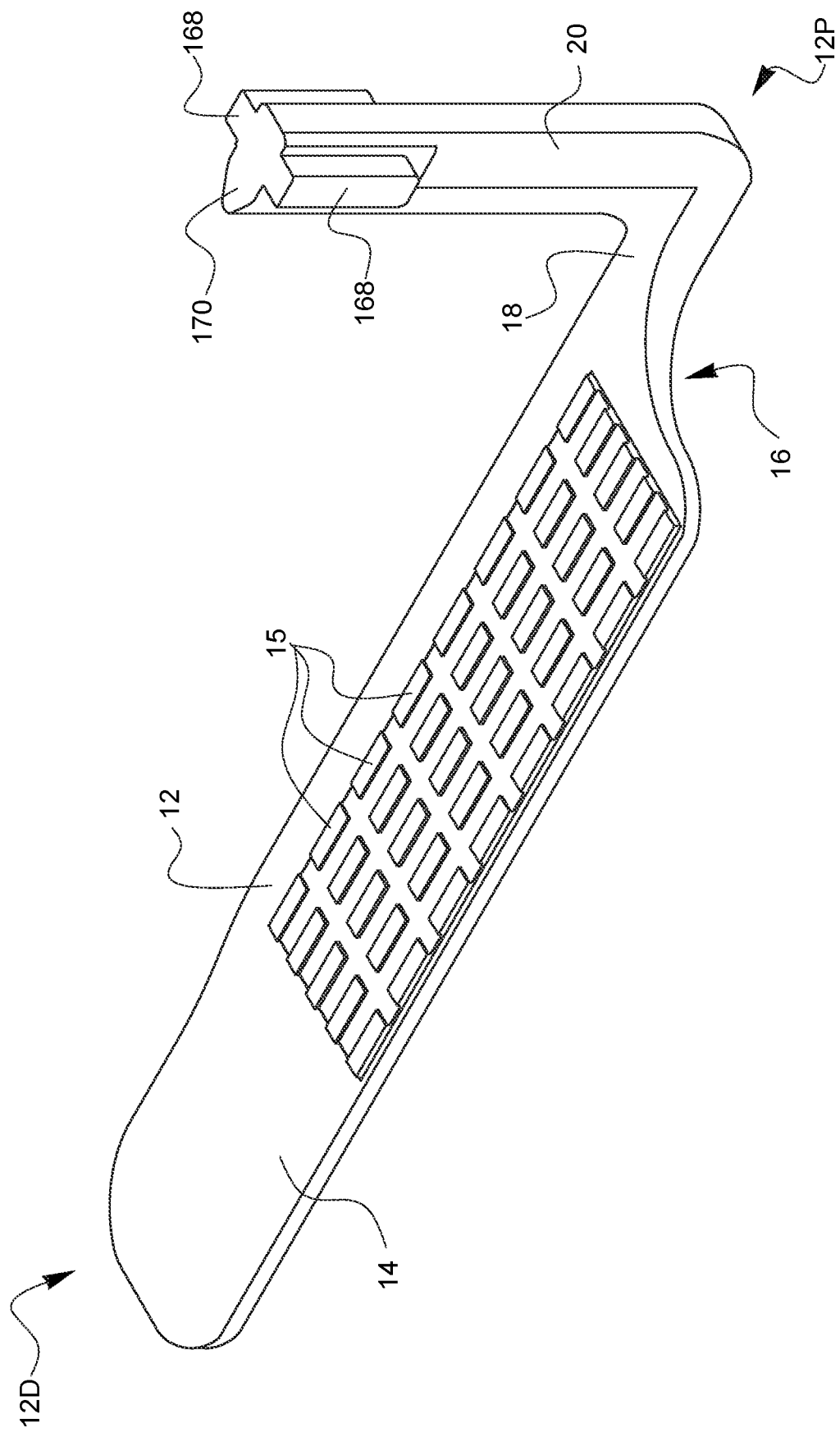
FIG. 5 is a perspective view of a right sternal ascender.

FIG. 5 is a perspective view of a right sternal ascender. This view illustrates the various features defined by the right sternal ascender 12. The right sternal ascender 12 defines a panel 14 having several textural features 15, a contralateral, or pertaining to the opposite side of targeted anatomical area, notch 16 at a proximal end 12P, a support beam, not shown here, traversing the underside of the panel 14, and a mounting post 20 for attachment to a sternal ascender assembly. The panel 14 has a rounded shape with a slight edge at a distal end 12D of the panel 14 of the right sternal ascender 12. Also defined by the post 20 are two opposing alignment and orientation features 168 configured to align, slide and lock the left sternal ascender 12 into the handle. These features 168 form a general t-shape, which are configured to fit into the aforementioned t-slot on the indicator handle 22. The use of this feature will be described further in regard to FIGS. 7A-7C. The post 20 also defines an angular front alignment feature 170 which is used to help align and place the left sternal ascender in an anatomical notch defined between a rib and sternum. This can serve as a tactile assist in placing the sternal ascender in an appropriate place when in use as part of a sternal ascender apparatus. While the embodiment shown has these characteristics, alternate embodiments may have other shapes or radiuses, and may or may not be sharpened. Still other embodiments may have other attachment features aside from the rectangular textural features 15 shown here, and may include other shaped features or none at all. Other embodiments of right sternal ascenders may be made of metal, plastic, composites, or mixtures or conbinations thereof. FIGS. 6A, 6B, 6C, 6D, 6E, and 6F are front, left side, right side, rear, top, and bottom elevational views, respectively, of the right sternal ascender of FIG. 5.

Figure 7A:
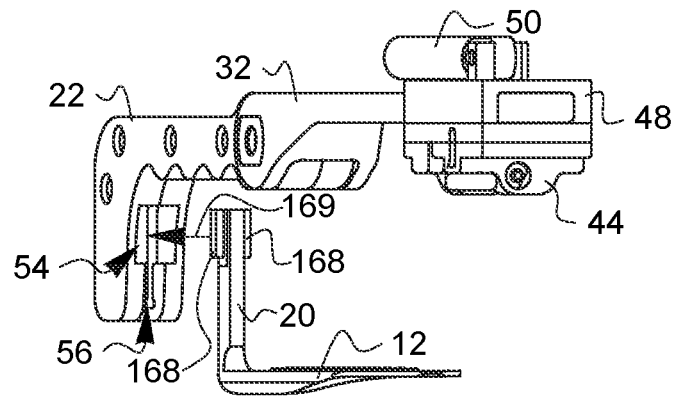
FIGS. 7A-7C are a series of perspective views illustrating operational steps showing the loading of the left sternal ascender of FIG. 5 into the sternal ascender apparatus of FIG. 1.
Figure 7B:
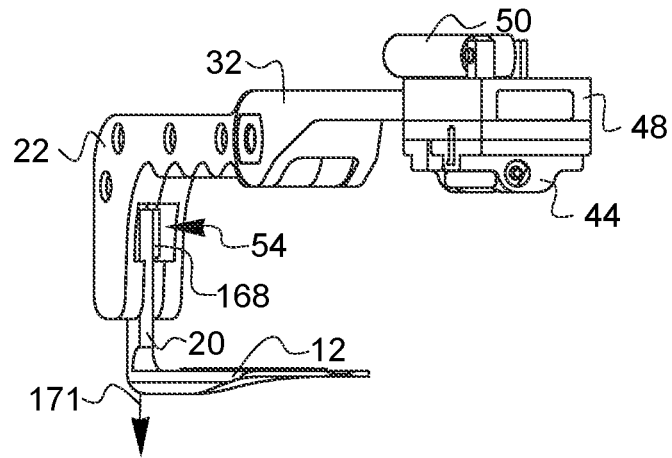
Figure 7C:
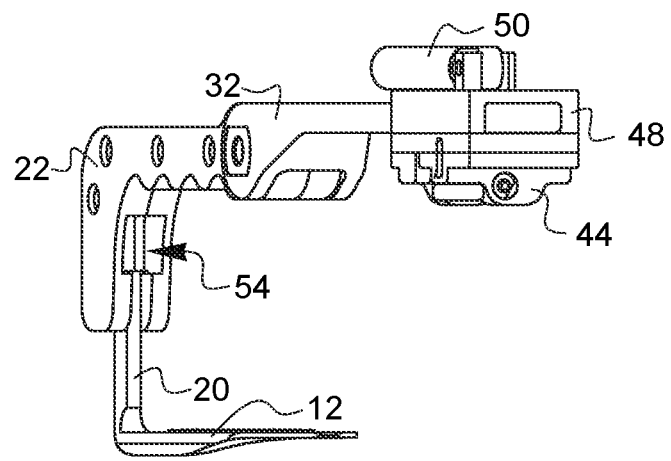

FIGS. 7A-7C are a series of perspective views illustrating operational steps showing the loading of the left sternal ascender of FIG. 5 into the sternal ascender apparatus of FIG. 1. The appropriate sternal ascender, left or right, is selected depending on the area of interest for a minimally invasive surgical procedure requiring the sternum of a patient to be lifted upward. FIG. 7A shows the right sternal ascender 12 aligned with and in proximity to the t-slot 54 of the indicator handle 22 of the sternal elevator apparatus 10 with the orientation features 168 on the post 20 of the right sternal ascender 12 moved towards direction 169 and fully inserted into the slot 54 of the indicator handle 22. Once inserted, as shown in FIG. 7B, the right sternal ascender 12 is pulled downward in direction 171 towards the seat 56 in the slot 54 of the indicator handle 22 to lock the right sternal ascender 12 into place. FIG. 7C shows the fully inserted and locked right sternal ascender 12 in the indicator handle 22.

Figure 8:
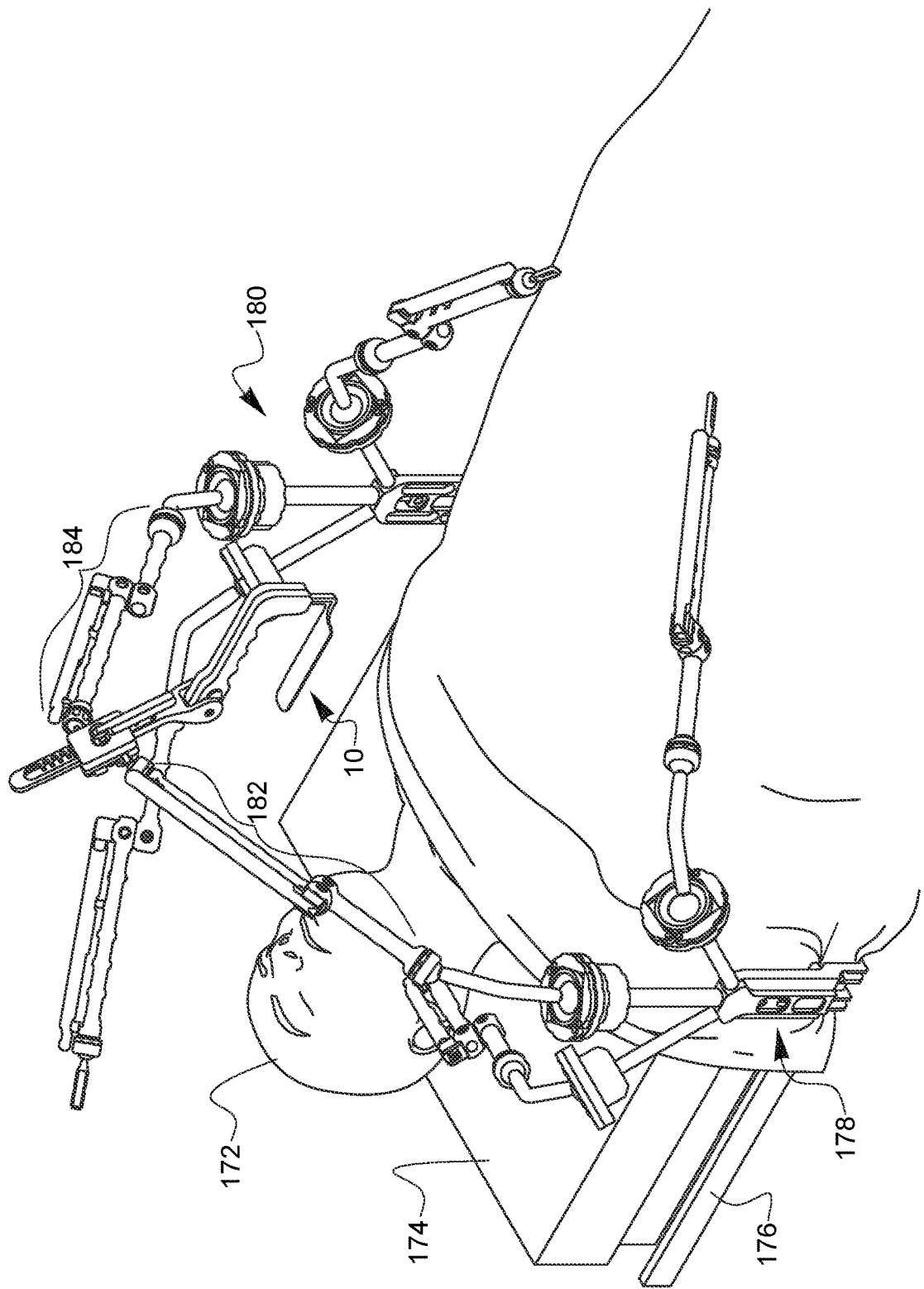
FIG. 8 is a perspective view of a surgical setting including the use of the sternal ascender apparatus of FIG. 1.

FIG. 8 is a perspective view of a surgical setting including the use of the sternal ascender apparatus of FIG. 1. In the illustrated surgical setting, an operating table 174 having a rail 176 and a patient 172 on the table 174 prepared for a surgical procedure are shown. Positioned on the rail 176 is a first surgical equipment holder apparatus 178 having a first central surgical equipment holder 182 attached to the first surgical equipment holder apparatus 178. The first surgical equipment holder apparatus 178 is attached to the sternal ascender apparatus 10 at the first adapter channel 46. On an opposite side of the table, a second surgical equipment holder apparatus 180 is attached to an opposite rail, which is not visible here. The second surgical equipment holder apparatus 180 has a second central surgical equipment holder 184 attached thereto and is also attached to the corresponding second adapter channel on the sternal ascender apparatus 10 on its opposite side, not visible here. Each of the first central surgical equipment holder 182 and the second central surgical equipment holder 184 can be utilized to position and hold one or more pieces of surgical equipment or tools such as the sternal ascender apparatus 10 or alternatively scope holders, cannulas, or other surgical implements during a minimally invasive or other surgical procedure. In this configuration, the first central surgical equipment holder 182 and the second central surgical equipment holder 184 are shown bridging over the patient 172 in order to firmly position the sternal ascender apparatus 10 in an initial centralized location relative to the patient 172 on the table 174.

Figure 9B:
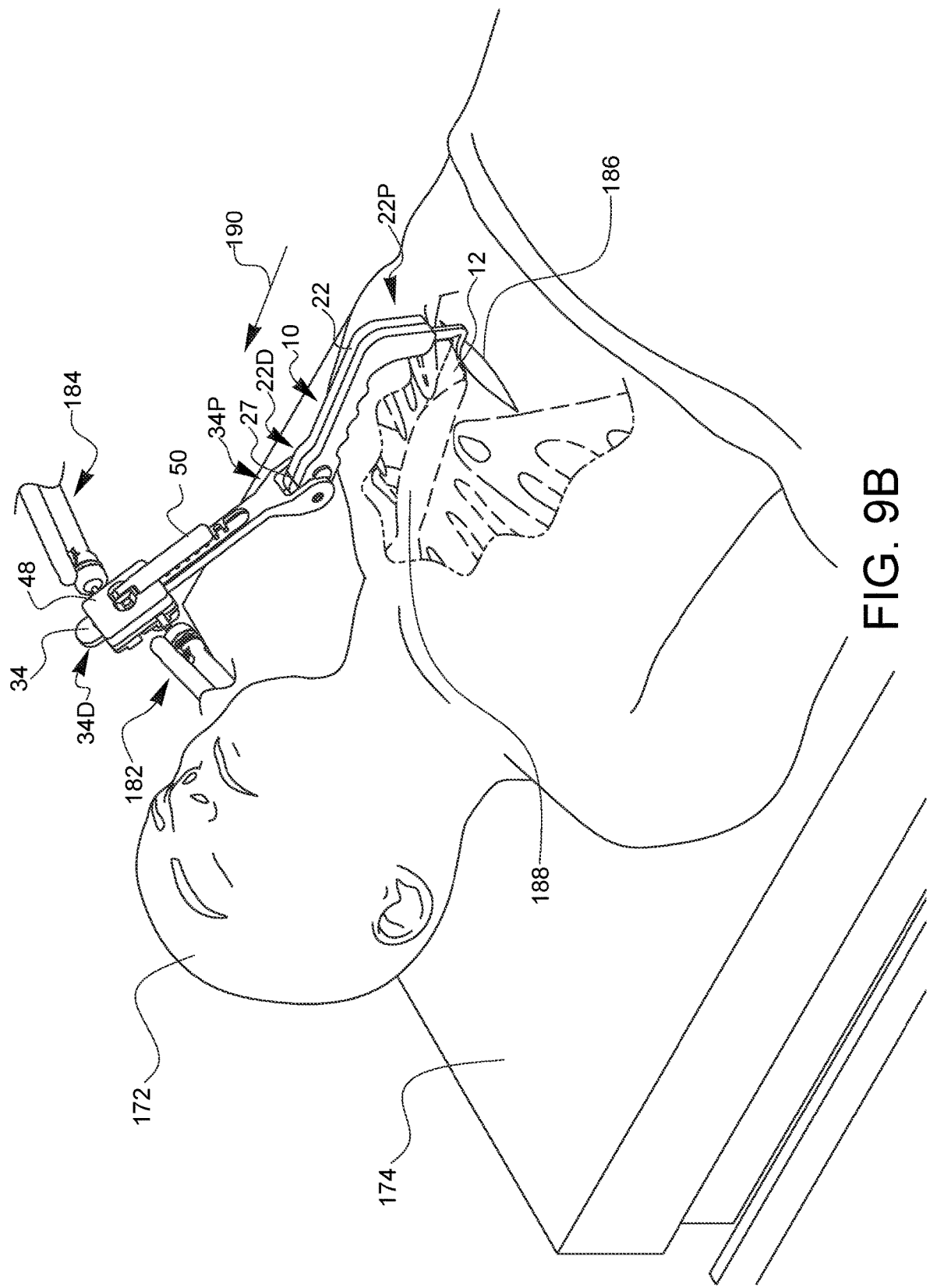
Figure 9C:
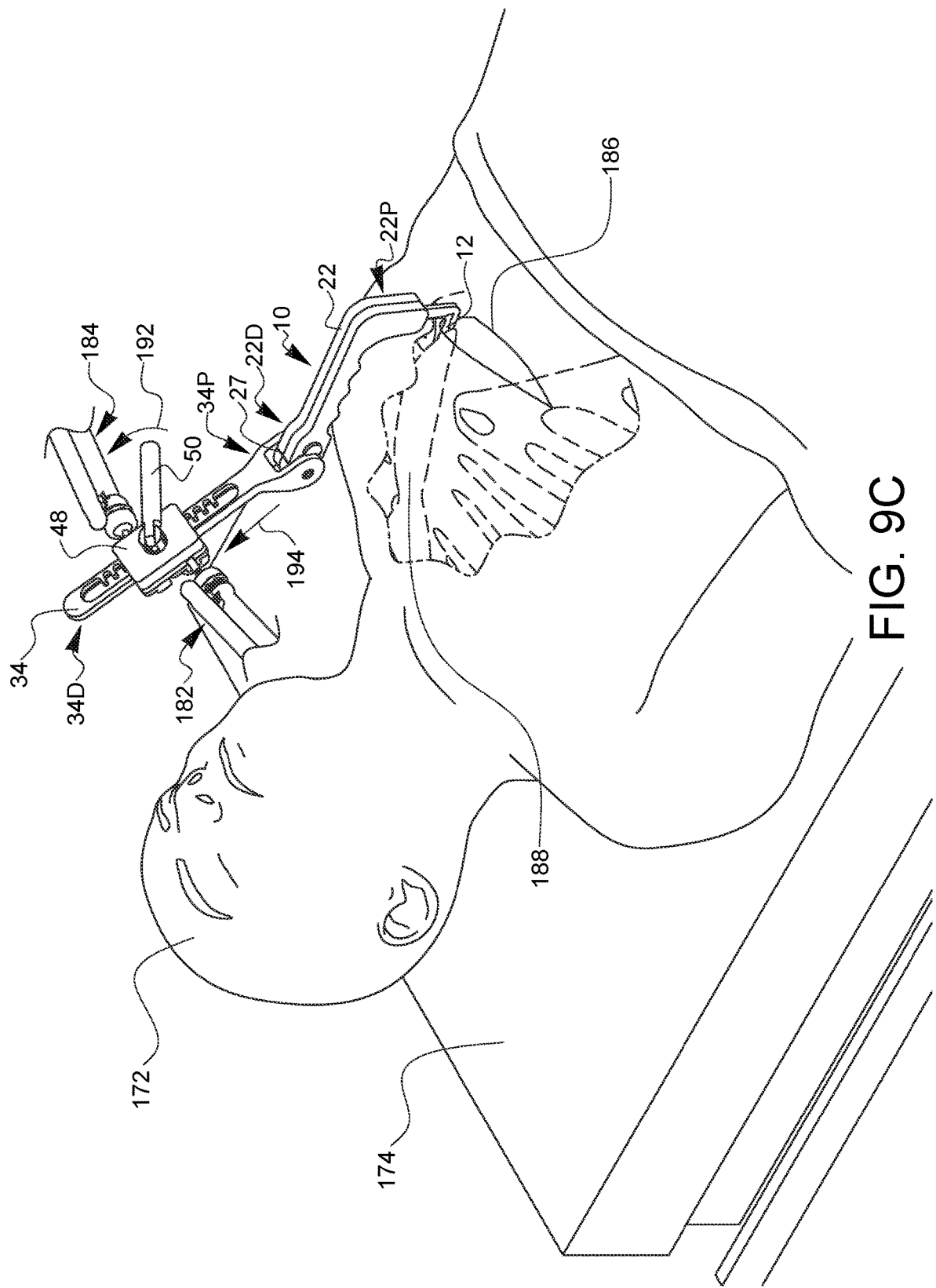
Figure 9D:
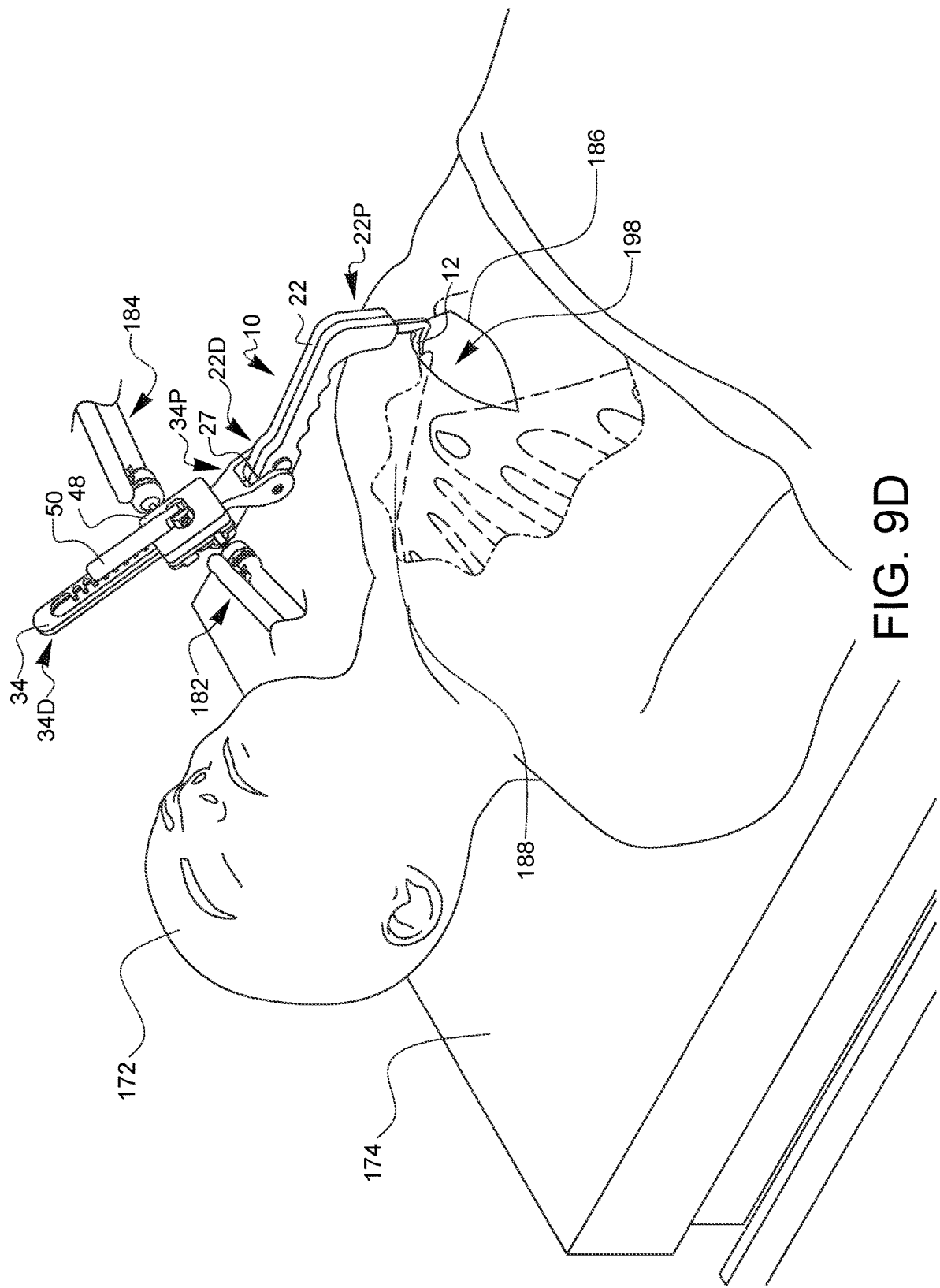

FIGS. 9A-9D are a series of perspective views illustrating operational steps of the use of the sternal ascender apparatus in a surgical context. In FIGS. 9A-9D, portions of the patient 172 are shown in cross-section and portions of various instrumentation are removed from view for the purposes of clarity. The patient 172 is shown prepped for a surgical procedure, having an incision 186 made at just below the xiphoid process at the sternal notch, near the sternum 188. The sternal elevator apparatus 10 is secured onto the first central surgical equipment holder 182 and the second central surgical equipment holder 184, which are firmly mounted onto the operating table 174. The upper rack housing 48, or the arch keystone is at the top of the toothed linear rack and thus enables subsequent movement of the rack 34 upward. The angle of the indicator handle 22 and therefore the sternal ascender 12 has been adjusted by pressing the pivot button or pressable switch 30 on the indicator handle 22, allowing movement of the indicator handle 22 relative to the linear actuator gear 34. As shown in FIG. 9B, the distal end 12D of the sternal ascender 12 is inserted in direction 190 into the incision 186 until the sternal ascender 12 is in a desired location along the sternum 188. The sternal ascender 12 is aligned with the anatomy of the sternum 188 by using the depth indicator 27 to gauge the location of the tip of the panel of the sternal ascender 12 within the chest. At this point, the first central surgical equipment holder 182 and the second central surgical equipment holder 184 are locked and secured into place after proper adjustment. FIG. 9C illustrates the swivel bar 50 being unlocked and moved counterclockwise 192 to raise the sternal ascender 12 and indicator handle 22 in direction 194, which applies retraction to the sternum 188 and creates the subxiphoid space 198 for access. A final state of this described procedure is illustrated in FIG. 9D, at which time the swivel bar 50 can be moved to a full up or down position to lock the gear housing 48 in place to prevent any further movement of the sternal ascender 12.

Various advantages of a sternal ascender assembly have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A sternal ascender assembly, comprising:
    a panel assembly, wherein a first portion of the panel assembly is configured to engage a portion of a patient's ribcage during a procedure;
    an indicator handle extending from a proximal end to a distal end along a handle axis, wherein a first portion of the indicator handle is configured to be grasped by a surgeon during the procedure, and wherein a second portion of the indicator handle is coupled to a second portion of the panel assembly;
    a linear rack extending from a first end to a second end along a rack axis, the second end of the linear rack being pivotably coupled to the distal end of the indicator handle, the linear rack comprising a plurality of teeth; and a housing movably coupled to the linear rack, the housing comprising a cylindrical gear configured to rotate relative to a portion of the housing, a portion of the cylindrical gear engaging a portion of the plurality of teeth of the linear rack to displace the linear rack relative to the portion of the housing when the cylindrical gear is rotated.

2. The sternal ascender assembly of claim 1, wherein the first portion of the panel assembly is an elongated support portion that extends from a proximal end to a distal end, and wherein a mounting post extends from the proximal end of the support portion such that the second portion of the panel assembly is a portion of the mounting post that is configured to be removably coupled to the second portion of the indicator handle.

3. The sternal ascender assembly of claim 2, wherein the support portion extends from the proximal end to the distal end along a support portion axis, and wherein the mounting post extends along an axis that is substantially normal to the support portion axis.

4. The sternal ascender assembly of claim 3, wherein the handle axis is substantially parallel to the support portion axis.

5. The sternal ascender assembly of claim 1, wherein the second end of the linear rack is coupled to the distal end of the indicator handle.

6. The sternal ascender assembly of claim 1, further comprising:
a pawl coupled to a fourth portion of the indicator handle; and
a fixed indexing gear coupled to a portion of the linear rack, wherein the fixed indexing gear is configured to interface with the pawl such that when one or more teeth on the pawl intermesh with one or more corresponding teeth of the fixed indexing gear, a position of the linear rack is locked relative to the indicator handle.

7. The sternal ascender assembly of claim 6, further comprising a switch coupled to the indicator handle and configured to defeat the pawl allow the fixed indexing gear to turn freely relative to the indicator handle.

8. A sternal ascender assembly, comprising:
a panel assembly, wherein a first portion of the panel assembly is configured to engage a portion of a patient's ribcage during a procedure;
an indicator handle coupled to a second portion of the panel assembly, the indicator handle comprising a grip portion that is configured to be grasped by a surgeon during the procedure;
a pawl coupled to a first portion of the indicator handle, the pawl including one or more teeth;
a linear rack extending from a first end to a second end along a rack axis, the second end of the linear rack being coupled to a second portion of the indicator handle, the linear rack including a engagement portion;
a fixed indexing gear including one or more teeth, the fixed indexing gear being configured to engage the pawl coupled to the first portion of the indicator handle such that when all or a portion of the one or more teeth of the pawl intermesh with all or a portion of the one or more corresponding teeth of the fixed indexing gear, a position of the linear rack is locked relative to the indicator handle; and
a housing movably coupled to the linear rack, the housing comprising a gear that is rotatably coupled to a portion of the housing and engages a portion of the engagement portion of the linear rack to displace the linear rack relative to the portion of the housing when the gear is rotated, thereby displacing the indicator handle and the panel assembly relative to the portion of the housing.

9. The sternal ascender assembly of claim 8, wherein the engagement portion of the linear rack is a plurality of rack teeth.

10. The sternal ascender assembly of claim 9, wherein a portion of the gear engages a portion of the plurality of rack teeth of the linear rack to displace the linear rack relative to the portion of the housing when the gear is rotated.

11. The sternal ascender assembly of claim 8, wherein the second end of the linear rack is pivotably coupled to a distal end of the indicator handle.

12. The sternal ascender assembly of claim 8, wherein the first portion of the panel assembly is an elongated support portion that extends from a proximal end to a distal end, and wherein a mounting post extends from the proximal end of the support portion such that the second portion of the panel assembly is a portion of the mounting post that is configured to be removably coupled to a third portion of the indicator handle.

13. The sternal ascender assembly of claim 12, wherein the support portion extends from the proximal end to the distal end along a support portion axis, and wherein the mounting post extends along an axis that is substantially normal to the support portion axis.

14. The sternal ascender assembly of claim 13, wherein the indicator handle extends from a proximal end to a distal end along a handle axis, and wherein the handle axis is substantially parallel to the support portion axis.

15. The sternal ascender assembly of claim 14, wherein the second end of the linear rack is coupled to the distal end of the indicator handle.

* * * * *